(12) United States Patent
Solomon et al.

(10) Patent No.: US 7,780,985 B2
(45) Date of Patent: *Aug. 24, 2010

(54) TABLETS HAVING A PRINTED SEPARATION MARK TO GUIDE BREAKING

(75) Inventors: Lawrence Solomon, Boca Raton, FL (US); Allan S. Kaplan, Boca Raton, FL (US)

(73) Assignee: Accu-Break Technologies, Inc., Plantation, FL (US)

( * ) Notice: Subject to any disclaimer, the term of this patent is extended or adjusted under 35 U.S.C. 154(b) by 1092 days.

This patent is subject to a terminal disclaimer.

(21) Appl. No.: 11/180,930

(22) Filed: Jul. 12, 2005

(65) Prior Publication Data

US 2007/0014852 A1   Jan. 18, 2007

(51) Int. Cl.
*A61K 9/44* (2006.01)
*A61K 49/00* (2006.01)

(52) U.S. Cl. .................. 424/467; 424/10.1; 424/10.2; 424/464

(58) Field of Classification Search ............... None
See application file for complete search history.

(56) References Cited

U.S. PATENT DOCUMENTS

| | | | |
|---|---|---|---|
| 2,052,376 A * | 8/1936 | Zellers ................. 424/467 |
| 3,128,226 A | 4/1964 | Rubin et al. |
| 5,002,775 A * | 3/1991 | Toya et al. ............. 424/10.2 |
| 5,436,026 A * | 7/1995 | Berta ................... 427/2.14 |
| 5,817,340 A | 10/1998 | Roche et al. |
| 6,086,919 A | 7/2000 | Bauer et al. |
| 6,183,778 B1 | 2/2001 | Conte et al. |
| 6,294,200 B1 | 9/2001 | Conte et al. |
| 6,309,668 B1 | 10/2001 | Bastin et al. |
| 6,919,373 B1 | 7/2005 | Lam et al. |
| 7,011,849 B2 | 3/2006 | Storm et al. |
| 2002/0132850 A1 | 9/2002 | Bartholomaeus |
| 2005/0038039 A1 | 2/2005 | Fanara et al. |
| 2006/0087051 A1* | 4/2006 | Bunick et al. ............ 264/109 |
| 2006/0280794 A1 | 12/2006 | Hamaguchi et al. |

OTHER PUBLICATIONS

H.A. Lieberman and L. Lachman, Pharmaceutical Dosage Forms, vol. 1, pp. 217-223, Marcel Dekker, Inc., New York, New York.
H.A. Lieberman and L. Lachman, Pharmaceutical Dosage Forms, vol. 1, pp. 217-223, Marcel Dekker, Inc., New York, New York, 1999.

* cited by examiner

*Primary Examiner*—Eric E. Silverman

(57) ABSTRACT

The invention provides a novel "separation marking" on a tablet as a means for assisting in the identification of a region on the tablet that is desired to be able to be broken from time to time. Said breaking allows production of smaller dosage forms known herein as tablettes. In a preferred embodiment, the separation mark will be a printed mark that is made on the tablet surface.

2 Claims, 3 Drawing Sheets

TABLETS HAVING A PRINTED SEPARATION MARK TO GUIDE BREAKING

CROSS-REFERENCE TO RELATED APPLICATIONS

Not Applicable

STATEMENT REGARDING FEDERALLY SPONSORED RESEARCH OF DEVELOPMENT

Not Applicable

INCORPORATION-BY-REFERENCE OF MATERIAL SUBMITTED ON A COMPACT DISK

Not Applicable

REFERENCE TO A MICROFICHE APPENDIX

Not Applicable

BACKGROUND OF THE INVENTION (1) Field of the Invention

This invention is concerned with the manufacture of pharmaceutical tablets adapted to be intentionally broken.

(2) Description of the Related Art

Pharmaceutical tablets ("tablets" herein) have long been produced with an indentation known as a score, which both locates and tends to physically assist in breaking said tablets into smaller units, called tablettes herein, that are intended to serve as dosage forms. Many tablets are not produced or may not be able to be produced with a score. It would be helpful if unscored tablets were marked in a manner that allowed identification of a suitable region of division when desired.

SUMMARY OF THE INVENTION

The invention provides a novel "separation marking" on a tablet that comprises a means for assisting in the identification of a region on the tablet that is desired to be able to be broken from time to time. Said breaking allows production of smaller dosage forms known herein as tablettes. In a preferred embodiment, the separation mark will be a printed mark that is made on the tablet surface with an edible ink that will provide a guide to breaking a tablet. In many preferred embodiments, said separation mark will allow location of a bisection of the tablet. The invention also provides a method of identifying a suitable breaking region of a pharmaceutical tablet by placing a separation mark on a tablet at, in or on a region where it is desired that breaking of the tablet is to be accomplished.

Accordingly, it is an object of the invention to provide an improved method of manufacturing tablets which are adapted for optional breaking so that more accurate breaking of both scored and unscored tablets may be obtained by breaking a tablet.

It is also an object of this invention to provide a separation mark on a relatively inactive part of the tablet.

These and other objects of the invention will become apparent from the appended specification.

DETAILED DESCRIPTION OF THE INVENTION

Figure 1:
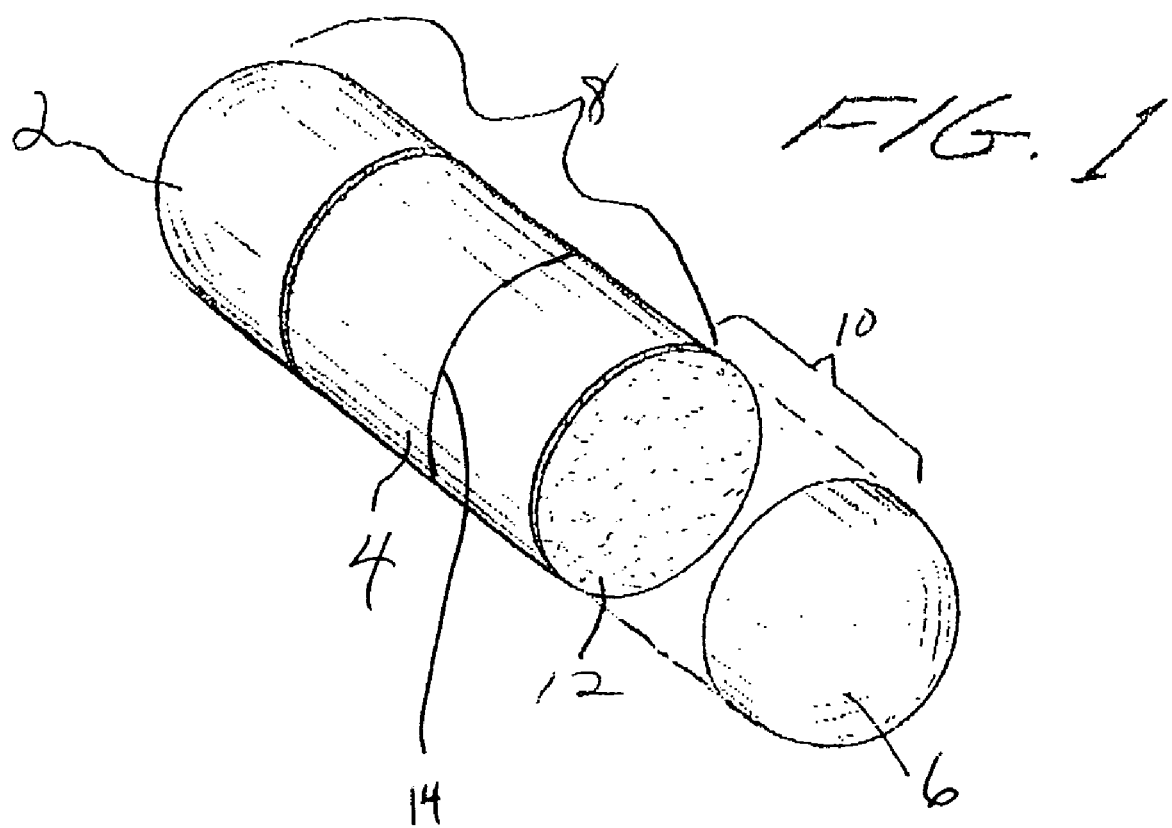
FIG. 1 is a partially exploded perspective view of a dosage form where two active segments contain an active ingredient and another segment having a printed separation mark is interposed between the two active segments.

Separation markings according to the invention include, without limitation:

Indicia applied by contact, spraying or printing in the form of a solid or dotted line at a desired breaking region on the tablet;

Indicia applied by printing a logo or series of logos, or such indications in appropriate language the word "Break," a symbol suggestive of breaking such as a representation of a scissors, a knife, tablet breaking device, or the like.

Other forms of separation marks may include, without limitation, application of one or more gelatin strips (bands, etc.) or strips applied by a biocompatible adhesive such as an Eudragit, shellac, or Hydroxypropyl methylcellulose.

The term "separation mark" or "separation marking" includes without limitation a continuous marking that is preferably linear, a discontinuous marking such as a dashed or dotted line, a raised addition to a tablet such a band of gelatin that may be applied in liquid or semi-liquid form, removable or non-removable tape, and the like. All embodiments may be provided in duplicate, triplicate, etc. For example, two or more printed lines may be utilized to delineate a region(s) between them suitable for optional tablet breaking.

A separation mark of the invention may be applied to the same surface of a tablet that contains a score. For example, a bisecting score could be present on a capsule-shaped tablet. Printed marks locating breaking regions that would, if broken precisely, create a quarter tablet could be added as well. Also, a separation mark could be on a different surface of the tablet than a score. For example, a three layer tablet could be formed in which the bottom punch contain an embossing that creates a score on the bottom of the tablet. Subsequently, a middle layer could be provided with a separation mark that would direct optional tablet breaking through said middle layer, separating the top and bottom layers from each other.

The separation marks may be applied at any suitable location on a tablet.

Generally, the indicia may be applied using edible inks and conventional printing techniques that are utilized to mark tablets with code numbers, logs and the like.

In preferred cases, tablets of the invention are provided to a patient, consumer, nurse, aide, etc. with a means of verification that a separation marking is indeed intended to delineate a guide to tablet breaking. Such means may be via printed product information on paper that accompanies the tablet upon sale, or may be via a convenient oral, electronic, recorded, etc. manner. Such instruction may not be necessary, however, as a printed mark that is on the center of a tablet will be apparent to a person of adequate sight to be a bisecting mark, and such a person who may have been intending to break said tablet into two equal parts would likely make use of said bisecting separation mark without specific instruction of its significance. Additionally, in cases in which a separation mark comprises the word "Break" or the words "Break Here," or comprises a scissors, said separation mark will tend to speak for itself.

Layered tablets may be produced that involve a middle layer that is formed from a granulation that optionally lacks an active pharmaceutical ingredient. Such a layer cannot be scored during tablet production. Providing a tablet a separation mark may be useful to guide optional tablet breaking through said layer.

Figure 2:
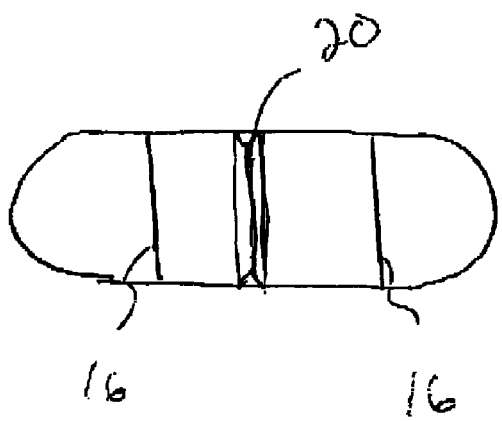
FIG. 2 is a top view of a tablet having a separation mark in the mid-point of the tablet.
Figure 3:
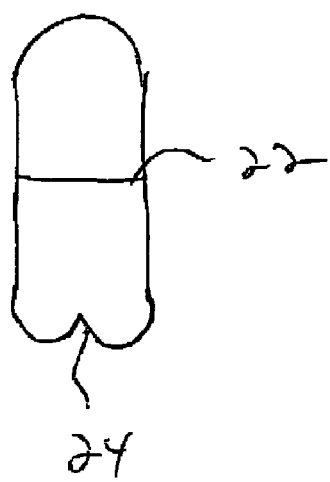
FIG. 3 is front view of a tablet having a separation mark at the mid-point of the tablet and a score placed on one end.
Figure 4:
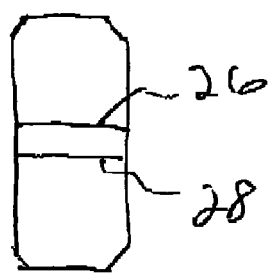
FIG. 4 is a top view of a tablet according to the invention which has two separation marks.
Figure 5:
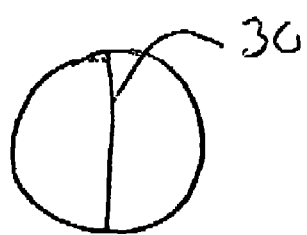
FIG. 5 is a top view of a tablet having a single separation mark.
Figure 6:
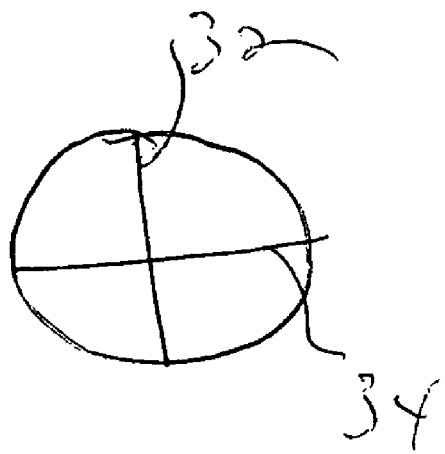
FIG. 6 is a top view of tablet according to the invention having crossed separation marks which divide the top of the tablet into four sections.
Figure 7:
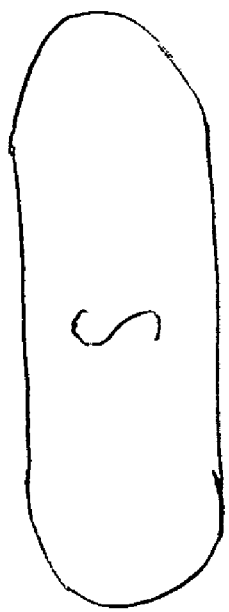
FIG. 7 is a top view of a tablet according to the invention which has a printed symbol as a separation mark.

As best shown in FIG. 1, a tablet having segments 2 and 6 and one pharmacologically inactive segment 4 is shown with space 10 that depicts the alignment of segment 8 and segment 6 which in use are joined to one another. Printed line 14 is located in segment 4 as a region where the breaking force is to be directed. The elongated segment 4 is long enough to be easily broken by hand. FIG. 2 shows a tablet having printed separation marks 16 and 18 and a score 20. FIG. 3 is a front view of a tablet having a printed separation mark 22 and a score 24. This tablet may be first broken at printed mark 22 and may thereafter be broken at score 24. FIG. 4 is a top view of a tablet having printed separation mark 26 and printed separation mark 28 spaced slightly apart to mark a breaking region between the two separation marks. FIG. 5 is a top view of a round tablet having a single printed separation mark 30 which marks the approximate mid-point of the tablet. FIG. 6 is a top view of a round tablet having printed separation mark 32 and printed separation mark 34 which are arranged in such a manner that the top surface is divided into four substantially equal parts. FIG. 7 is a top view of a tablet where a printed symbol which is a stylized letter "S" is used as a printed separation mark to identify the approximate mid-point of the tablet as a breaking region. This type of a separation mark may comprise a logo which is applied alone of as a plurality of marks that form a linear pattern.

The invention also includes the method of administration of a pharmaceutical to a patient, mammal, or other animal in need of said pharmaceutical where a region on a pharmaceutical tablet is provided with a separation mark or marks and the tablet is broken through, by, or between said mark or marks to form one or more parts of said tablet which are designated herein as "tablettes". The method of administration is completed by having the patient ingest the tablette formed from breaking the tablet.

The invention claimed is:

1. A method for administering a part of a pharmaceutical tablet to a subject in need of said part of said pharmaceutical tablet where said pharmaceutical is contained in a pharmaceutical tablet bearing one or more printed indicia selected from the group consisting of a solid line, a dotted line or a symbol, said indicia being located at a region where said pharmaceutical tablet is to be broken; breaking said tablet through or between said one or more indicia to form a tablette, and administering said tablette to the subject.

2. A method for administering a part of a pharmaceutical tablet to a subject in need of said part of said pharmaceutical tablet where said pharmaceutical is contained in a pharmaceutical tablet bearing one or more indicia selected from the group consisting of a dotted line or a symbol, said indicia being located at a region where said pharmaceutical tablet is to be broken; breaking said tablet through or between said indicia to form a tablette, and administering said tablette to the subject.

\* \* \* \* \*